United States Patent [19]

Gustafsson et al.

[11] Patent Number: 4,579,661

[45] Date of Patent: Apr. 1, 1986

[54] PROCESS IN THE PURIFICATION OF BIOLOGICALLY ACTIVE SUBSTANCES

[75] Inventors: Sture J. Gustafsson, Upsala; Per O. Hedman, Upplands Väsby; Torbjörn G. I. Ling; Bo G. Mattiasson, both of Lund, all of Sweden

[73] Assignee: Pharmacia AB, Upsala, Sweden

[21] Appl. No.: 681,995

[22] PCT Filed: Apr. 27, 1984

[86] PCT No.: PCT/SE84/00159

§ 371 Date: Oct. 26, 1984

§ 102(e) Date: Oct. 26, 1984

[87] PCT Pub. No.: WO84/04309

PCT Pub. Date: Nov. 8, 1984

[30] Foreign Application Priority Data

May 2, 1983 [SE] Sweden .............................. 8302483

[51] Int. Cl.[4] .............................................. B01D 15/08
[52] U.S. Cl. .................................. 210/635; 210/638; 210/927
[58] Field of Search ................ 210/634, 635, 638, 927

[56] References Cited

U.S. PATENT DOCUMENTS

| 3,996,132 | 12/1976 | Mateos et al. | 210/634 |
| 4,207,200 | 6/1980 | Muller et al. | 422/56 |
| 4,268,395 | 5/1981 | Stewart | 210/634 |
| 4,406,865 | 9/1983 | Fuller | 210/638 |
| 4,464,165 | 8/1984 | Pollard, Jr. | 210/635 |

FOREIGN PATENT DOCUMENTS 144679 7/1976 Denmark .
2252351 6/1975 France .

OTHER PUBLICATIONS

Chemical Abstracts, vol. 78, 1983, p. 188, No. 120936s.

*Primary Examiner*—John Adee
*Attorney, Agent, or Firm*—Fred Philpitt

[57] ABSTRACT

The invention is concerned with purification of a biologically active substance with the aid of a system of at least two immiscible aqueous phases; the process of the invention involves binding said substance to particles which have an affinity for said substance and distribute predominantly quantitative into one of said phases, and subsequently liberating said substance from said particles after separating the particle-containing phase from the other phase or the other phases.

6 Claims, No Drawings

PROCESS IN THE PURIFICATION OF BIOLOGICALLY ACTIVE SUBSTANCES

The present invention is concerned with a process in the purification of a biologically active substance with the aid of a system of at least two immiscible aqueous phases.

When a solution contains biologically active substances such as for example peptides, proteins and other biomolecules it is desirable to have ways and means for isolating individual components therefrom, and consequently a major number of separation methods have been developed for various different systems of biomolecules. For large-scale separations, a number of techniques employing columns are now being used extensively. In these methods the solution is passed along a gel bed; in passing along the bed the individual components present in the solution will be delayed in different degrees, depending on their molecular size (gel filtration), or will bind to groups present in the gel, depending on electric charge (ion exchange chromatography), or will bind due to biospecific affinity to ligands immobilized in the gel (affinity chromatography). These methods often require long separation times since the amount of solution to be passed through the column is relatively large, and moreover the range of practical applicabilities of such methods will be limited because of the requirement that all components should be present in a solubilized form; for if solids are present these will greatly tend to obturate the gel bed. Therefore, if any such non-dissolved material is present in a biological fluid sample an extra preliminary separation step is required, such as e.g. filtration and/or centrifugation.

A method found to have potential advantages in connection with large-scale purifications involves the utilization of systems containing at least two liquid phases having different polar properties, in which case different components of the sample assume different patterns inter se of their respective distribution among the phases. In view of the fact that biological substances often require mild conditions of treatment in order to avoid losing their activity the phases employed are in the first place aqueous phases, sometimes in conjunction with mild organic solvents.

Separation systems of this type may contain aqueous solutions of (1) at least two polymers
(2) at least one polymer and at least one salt
(3) at least one polymer and at least one organic solvent.

Systems according to item (1) consisting of at least two aqueous polymers have been described by for example Albertsson, P. A., in "Partition of Cell Particles and Macromolecules" (Almquist & Wiksell, Stockholm, and John Wiley & Sons Inc., New York 1971); in addition to water such systems may contain for example the following combinations of water-soluble polymers: polyethylene glycol/dextran; polypropylene glycol/dextran; polyethylene glycol/polyvinyl alcohol; polyethylene glycol/Ficoll ® (copolymer of sucrose and epichlorohydrin, from Pharmacia Fine Chemicals, Uppsala, Sweden); polyvinyl alcohol/dextran; methyl cellulose/dextran; polypropylene glycol/polyvinyl pyrrolidone; charged polyethylene glycol/dextran; polypropylene glycol/methoxypolyethylene glycol; polypropylene glycol/polyvinyl alcohol; polypropylene glycol/hydroxypropyl dextran; polyethylene glycol/polyvinyl pyrrolidone; polyethylene glycol/starch; and polyvinyl alcohol/methyl cellulose. Additional combinations of these and also other polymers are well known from the literature. Among the aforesaid combinations, the two-phase systems comprising dextran as their more polar phase have been studied most extensively; but the comparatively high price of dextran is a limiting factor for the large-scale utilization of the method.

In systems according to the above item (2) containing aqueous solutions of at least one polymer and at least one salt, the polymer may be selected from among those mentioned above and the salt may be a water-soluble organic or inorganic salt such as e.g. phosphate or sulfate, for example potassium phosphate and magnesium sulfate. The more polar phase which in this case is a salt solution can be prepared at low costs, so this method will be well suited for economically attractive large-scale applications.

As can be seen from item (3) above one of the phases may also consist of an organic liquid; this should be chosen from among liquids that will not adversely affect the biological molecules present in the separation system. Examples of such liquids may be alcohols of a type such as propyl alcohol, glycerol, butanoxyethanol.

The separation method will be discussed below as applied to a two-phase system containing two aqueous phases in accordance with items (1) and (2) above, although, as has been mentioned above, more than two phases may be present, and also non-aqueous phases may be present in the system. In this method contact is established between the two phases one of which (usually the more polar one) contains the mixture of components to be separated. Different biomolecules in this mixture will have different tendencies to migrate from their original phase into the other phase; there will thus result a phase separation of the components of the mixture. For this separation to be optimum, the "target" component or components to be isolated must be found to be present quantitatively in either one of the phases while the bulk of the remaining components must be found to be present in the other phase. Only rarely, however, will the distribution ratio encountered be so favorable that this method can be employed in just this form as described originally. Far better distribution ratio and concomitantly much better yields and purity are obtained with a system containing a soluble ligand having an affinity for the target component. In this case the factor determining the efficiency with which that component is enriched in one of the phases will be the distribution characteristics of the ligand-component complex in the phase system. For instance, Flanagan, S. et al (J. Biol. Chem. 250(4) (1975), 1484–9 and 251(3) (1976), 858–865) have shown the advantages that can be obtained by working in a dextran/polyethylene glycol two-phase system employing soluble ligands which are coupled covalently to one of the polymers present. Müller et al in U.S. Pat. No. 4,207,200 have described nucleic acid separation in a two-phase system of polyethylene glycol and dextran with the aid of soluble ligands derivatized with polyethylene glycol and having an affinity for nucleic acids. The disadvantages inherent in the use of soluble ligands of the type described in the literature reside in the potential difficulty of obtaining a quantitative distribution of the ligand-component complex into one of the phases—even in those cases where the ligand actually does have favorable distribution characteristics: Contributions from in particular larger biomolecules may cause the ligand-component complex to assume a distribution pattern less favorable than that of the ligand itself. Moreover, additional separation steps are required for the subsequent isolation of the target component from the ligand to which it is bound.

We have now found, in accordance with the present invention, that the aforesaid problems inherent in purification processes employing two-phase systems are eliminated efficiently if the ligands employed are insoluble particles which have an affinity for the component to be purified and have a sufficiently high coefficient of distribution for one of said phases to cause said particles to be distributed quantitatively into said one phase. The particles are inert, meaning that they do not react with components in the system in any way other than by the binding between specific groups on the particle and substances that have an affinity for those groups. The term "quantitative distribution", in the sense as employed here, does not exclude the possibility that a minor portion of the total amount of particles may disobey the distribution behavior assumed by the majority of the particles and will e.g. adhere to glass surfaces.

Particles that have been distributed into an upper phase will settle on the bottom surface of this phase if the density thereof is sufficiently high.

The biologically active substance is caused to bind, "tethered", to the particles which according to their distribution characteristics concentrate into one of the phases. That phase is then separated from the other phase, and the particles are filtered off and washed. Thereafter the substance is released from the particles in a suitable milieu. The particle size is not critical for the performance of the purifying process according to this invention. The upper limit for the particle size is set by the weight of the particles and by long diffusion paths and, concomitantly, adsorption times. Small particles provide for quicker adsorption of the substance and greater total surface area, but in a subsequent elution procedure in a column the flow resistance will increase in a known manner, more and more with decreasing particle size. The diameter of the particle is preferably of the order of 1 to 1000 μm. Because of the size of the particle as compared to that of the biomolecules to be separated the distribution characteristics of the particle will not change in any significant manner when the target component binds to the particle; and this is still true also in case the particle has several binding sites for that component. Particles that are suitable for use in the purification process according to the invention include for example such matrices, "gels", as are known from chromatographic column separations, e.g. beads based on for instance cross-linked dextran, agarose, cross-linked agarose, cellulose, cross-linked cellulose and cross-linked starch. Cross-linking is effected in order to increase the rigidity of the matrix. Other examples are beads of polyacrylamide, polymethacrylate and hydrophilized polystyrene. However, these and alternative choices of particles are well known and readily evident to a person skilled in the art.

If the particles do not per se have a sufficiently high distribution coefficient for the desired phase they have to be provided with groups effective to change their polar properties in a desired manner, that is, these properties should be made to be similar to those of the phase into which one would like the particles to be directed. For increasing the hydrophilic properties of a particle, derivatizing of that particle is effected with for example hydroxyl, carboxyl, amino or sulfo groups. If it is desired that the particle acquires an increased hydrophobicity, derivatizing may be carried out with e.g. polymers of the polyethylene glycol and polypropylene glycol types. Also of course other substituents might be used, for example substituents containing optionally substituted hydrocarbon residues, e.g. hydroxypropyl groups; the particular selection of suitable groups will be directed by basic knowledge of the hydrophilic-hydrophobic properties of the structure.

For derivatizing the particle with groups providing the desired polarity properties, and with specific groups for bringing about subsequent binding of the target component, it will be possible to employ any of the coupling methods that are known in connection with various chromatography techniques. Among such coupling methods may be mentioned, especially, CNBr coupling, epoxy coupling, and triazine coupling. For many years these methods have been in use for covalent coupling of e.g. biomolecules and polymers to inert matrices in various affinity chromatography contexts. Many practical embodiments and uses of this technique have been described, and on the basis of this technology it will be readily apparent which substances/groups can be immobilized on the inert particle in order to bestow on said particle a biospecific affinity for certain special components. Examples of such substances/groups are antibodies, antigens, enzymes, enzyme substrates, lectins or other affinity ligands.

The affinity of the particles for the biologically active substance may also be an electrostatic-type affinity, the particles in this case having charged groups on their surface. Anion exchange groups such as for instance quaternary or tertiary amino groups, and cation exchange groups such as for instance carboxyl and sulfo groups are well known from ion exchange chromatographic technology.

It is also possible of course to synthesize a particle that is suitable for purification processes according to the present invention, in a manner such that the synthesis is carried out in a mixture containing in addition to the matrix material also ingredients that will bestow the desired hydrophilic/hydrophobic properties on the particle and will moreover introduce the specifically binding groups. In this case, then, the particle will have the desired properties already from the very outset, and no extra derivatizing steps will be required.

A good illustration of the advantages of the present method is given when the method is applied to the purification of a substance produced in a microorganism, e.g. a bacterial cell. The substance may be a product naturally produced in the cell, or may be a product which is formed after a specific DNA sequence has been inserted, for example by recombinant DNA technology. In cases where the cell does not secrete the substance the cell wall has to be destroyed in order for the substance to be released; this means that the substance has to be isolated in a mixture of solid cell debris and a very great number of solubilized biomolecules. To this cell homogenate are added particles derivatized with for example polyethylene glycol and having an affinity for the said substance. Then—in the case of a system of type (2) above—a salt is added such as for example potassium phosphate. When the cell homogenate is thereafter contacted with an aqueous solution of polyethylene glycol a two-phase system is formed and the polyethylene glycol derivatized particles will migrate into the upper, polyethylene glycol phase. The other components will predominantly remain in the lower, more polar salt phase. The upper phase, which may comprise an only small volume because of the favourable distribution conditions, is separated from the lower phase, and the aqueous solution of polyethylene glycol is filtered off. The particles are then washed for the purpose of removing other components that may have migrated into the upper phase. For releasing the target substance from the particles a change in the existing conditions is effected so as to weaken the substance-particle bond; this may be achieved by for instance a change in pH.

Conveniently, the liquid phase containing the particles is directly passed down into an empty column provided with a bottom grid, whereupon the column with the particles thus retained is connected to a chromatographic system washed and eluted with a suitable solution. This may be accomplished by directly applying techniques as described in the literature for the elution of components in affinity and ion exchange chromatography technologies.

The method will be illustrated below by some non-limitative examples of: preparation of activated particles; coupling of ligands to such particles; and separations in two-phase systems.

EXAMPLE 1

Preparation of activated particles
(a) Coupling polyethylene glycol to Sepharose ® 6B 16 g of polyethylene glycol 4000 (Merck) were dissolved in 50 ml distilled water at 40° C. Then the pH was adjusted to about 12.5 with NaOH, whereupon 20 g of washed Epoxyactivated Sepharose ® 6B (Pharmacia Fine Chemicals, Sweden) were added. After an 18-hour period of shaking at 40° C., 15 ml of ethylene glycol were added; and after a further 4 hours the particles were washed again with distilled water and 0.05M phosphate buffer pH 7.

(b) Coupling methoxypolyethylene glycol to Sepharose ® 6B 12 g methoxypolyethylene glycol 3000 (Hoechst) were coupled to Epoxyactivated Sepharose ® 6B in the manner as described in Example 1(a).

(c) CNBr activation of polyethylene glycol—Sepharose ® 6B 1.00 g CNBr was dissolved in 30 ml of distilled water, and the reaction vessel was then set into an ice bath. Next followed an addition of 15 ml of gel that had been washed with cold distilled water; and after adjustment of the pH to 11.3 with NaOH, activation was carried out during a period of 6 minutes. The product was then washed with distilled water, 0.25M citric acid pH 3, 0.005M citric acid pH 3 and distilled water in succession.

(d) CNBr activation of methoxypolyethylene glycol—Sepharose ® 6B

Methoxypolyethylene glycol—Sepharose ® 6B was activated in the same manner as in Example 1(c).

(e) Tresyl activation of polyethylene glycol—Sepharose ® 6B

Polyethylene glycol 20 000 (Merck) was coupled to Epoxyactivated Sepharose ® 6B in a manner analogous to that described in Example 1(a). 30 ml of gel were washed with distilled water and then transferred to acetone. Activation was carried out with 1.2 mmol 2,2,2-trifluoroethane sulfonyl chloride in a mixture of 60 ml acetone and 2.4 ml pyridine during a period of 12 minutes. The product was washed on a glass filter with cold acetone followed by 1 mM HCl.

(f) Epoxy activation of polyethylene glycol—Sepharose ® 6B 27 ml of gel according to Example 1(a) were washed with distilled water. After this washing step, 35 ml of 0.45M NaOH solution containing 70 mg $NaBH_4$ were added, followed by 15.6 ml 1,4-bis(epoxypropoxy)butane. The reaction was carried out during a 3-hour period at 24° C., whereupon the product was washed with distilled water.

EXAMPLE 2

Coupling ligands to activated particles, said ligands having an affinity to biologically active substances 2(a) Coupling gamma-globulin to polyethylene glycol—Sepharose ® 6B 10.9 ml of tresyl activated polyethylene glycol—Sepharose ® 6B from Example 1(e) were reacted with 180 mg gamma-globulin (Sigma) in buffer pH 8.7 (0.1M $NaHCO_3$, 0.5M NaCl) for 4 hours with agitation, whereupon the mixture (a total of 20 ml) was left standing overnight at 4° C. The product was then washed, in alternating succession, with 0.1M acetate buffer pH 4.0 (0.5M NaCl) and 0.2M carbonate buffer pH 8.3 (0.5M NaCl). Storage in 0.025M phosphate buffer pH 7.2.

2(b) Coupling albumin to polyethylene glycol—Sepharose ® 6B 19.1 ml of tresyl activated polyethylene glycol—Sepharose ® 6B from Example 1(e) were reacted with 320 mg of bovine serum albumin (Sigma) under the same conditions as in Example 2(a) (total volume 59.9 ml).

2(c) Coupling gamma-globulin to methoxypolyethylene glycol—Sepharose ® 6B 12 g of CNBr activated methoxypolyethylene glycol—Sepharose ® 6B were reacted with 200 mg gamma-globulin (Sigma) in 10 ml of 0.1M carbonate buffer pH 8.3 (0.5M NaCl) for a period of 3 hours with agitation. After a further 2-day period at 4° C. the product was washed, in alternating succession, with 0.1M acetate buffer pH 4.0 and 0.1M carbonate buffer pH 8.3 (in both cases 0.5M NaCl). The product was stored in 20 mM phosphate buffer at pH 7.0.

2(d) Coupling Cibacron ® blue to polyethylene glycol—Sepharose ® 6B 25 ml of the settled polyethylene glycol—Sepharose ® 6B product of Example 1(a) were reacted for 100 minutes with 1 g of Cibacron ® blue F3G-A in 25 ml of distilled water containing 0.09 g KOH at 80° C. The product was washed with distilled water, 0.025M phosphate buffer pH 7.4, distilled water, ethanol, distilled water and phosphate buffer in succession.

EXAMPLE 3

Binding biologically active substances to particles. Purification in two-phase system 3(a) Binding protein A to gamma-globulin—polyethylene glycol—Sepharose ® 6B 1.5 ml gamma-globulin—polyethylene glycol—Sepharose ® 6B from Example 2(a) was added to a solution of 2.5 mg of protein A (Pharmacia Fine Chemicals, Sweden) in 0.1M phosphate buffer pH 7.1, whereupon the reaction vessel was rotated for 1 hour. After addition of polyethylene glycol 4000 and an aqueous solution, pH 7, of $K_2HPO_4$ and $KH_2PO_4$, the mixture was agitated. After this treatment a two-phase system formed having the composition phosphate 11.0% (w/w), polyethylene glycol 19.5%, and distilled water 69.5%. The upper phase which contained the gel particles was transferred to an empty column having a bottom grid, whereupon the gel particles were washed with 0.1M phosphate buffer pH 7.2. Elution with 0.1M glycine pH 3 released 0.8 mg of protein A from the gel particles. Purity was checked by means of electrophoresis in polyacrylamide gel PAA 4/30 (Pharmacia Fine Chemicals, Sweden).

3(b) Binding protein A to gamma-globulin—polyethylene glycol—Sepharose® 6B (I) and to gamma-globulin13 methoxypolyethylene glycol—Sepharose® 6B (II)

1 ml of gel suspension containing about 0.6 ml of settled gel produced according to Example 2(c) (or in an analogous manner) was added in two parallel experiments to a solution of 1.94 mg protein A in 0.1M phosphate buffer pH 7.1. The reaction vessel was rotated for 2 hours, whereupon followed additions of polyethylene glycol 4000, polyethylene glycol 1540, and an aqueous solution of $KH_2PO_4$ and $K_2HPO_4$ pH 7. A two-phase system formed having the composition phosphate 9.4%, polyethylene glycol 4000 13.1%, polyethylene glycol 1540 4.9%, distilled water 72.6%.

The polyethylene glycol phase containing the gel particles was transferred to an empty column having a bottom grid, whereupon the gel particles were filtered off and washed with phosphate buffer. Elution with 0.1M glycine pH 3 yielded 1.24 mg of protein A (I) and 1.40 mg of protein A (II) respectively. Purity was checked by means of electrophoresis in polyacrylamide gel. The experiment was then repeated with polyethylene glycol—Sepharose® 6B particles and with methoxypolyethylene glycol—Sepharose® 6B particles, that is, with particles lacking a biospecific affinity ligand. In these cases no protein A could be detected upon elution with glycine.

A test was run for checking whether any gamma-globulin was released from the gel particles employed in the two-phase separation procedure; for this purpose the particles were incubated for 16 hours with 0.1M glycine pH 3. No gamma-globulin leakage was detectable (no absorbance at 280 nm).

3(c) Binding albumin to Cibacron® blue—polyethylene glycol—Sepharose® 6B (I) and to Cibacron® blue—methoxypolyethylene glycol—Sepharose® 6B (II)

4 ml of gel suspension containing about 2 ml of settled gel produced according to Example 2(d) (or in an analogous manner) were added in two parallel experiments to a solution of 28.2 mg albumin in 0.025M phosphate buffer pH 7.2. The reaction vessel was rotated for 45 minutes, whereupon the gel particles were allowed to settle. The concentration of albumin in the supernatant was measured, and on the basis of this concentration the amount of albumin bound to the gel particles could be calculated to be 7.0 mg in case (I) and 9.85 mg in case (II). Polyethylene glycol 4000, dextran T500 and distilled water were added, and a two-phase system formed having the composition polyethylene glycol 4000 6.0%, dextran T500 7.2%, distilled water 86.8%. The polyethylene glycol phase containing the gel particles was transferred to a column having a bottom grid, and after washing of the gel particles with 0.025M phosphate buffer, pH 7.2, an amount of 7.24 mg albumin (I) and of 9.26 mg albumin (II), resp., could be eluted from the column. These findings are in good agreement with the aforesaid calculated values of the amounts of particle-bound albumin.

3(d) Binding hexokinase to Procion Red HE2B—starch 2 g of Procion Red HE2B (ICI, England) and 3 g of disodiumcarbonate were dissolved in 100 ml of distilled water. Then 20 g of starch beads (potato flour, "potatismjöl, extra prima" from Sveriges Stärkelseproducenters Förening, Karlshamn, Sweden) were added under agitation. The temperature was raised to 50° C. and the reaction was carried out during a 16-hour period. The product was washed with distilled water until the solution was colourless and then 3 times with a 10 mM sodiumphosphate buffer, pH 6.4.

15 μl of the derivatized starch beads were mixed with 50 μl of hexokinase from *Saccharomyces cerivisiae* (Sigma and our own preparation, respectively) and 900 μl of a phase system containing 15,0% Maltrin M-100 (Grain Processing Corp. Muscatine, Iowa, US) and 5% PEG-8000 and 10 mM sodiumphosphate (pH 6.4).

The phase system was thoroughly mixed and was then allowed to separate during one hour. The beads were distributed to the PEG-phase which was removed and transferred to a column. Elution of the column at pH 8.5 released the enzyme from the beads. The yield was 32%.

3(e) Binding albumin to Cibacron® Blue F3GA-cellulose

Microcrystallin cellulose (Merck) was reacted with Reactive Blue II (Sigma) in a manner analogous to that described in Example 3(d).

50 μl of albumin (Sigma) and 50 μl of the derivatized cellulose beads were mixed with 900 μl of a phase system containing 15.0% Maltrin M-100 and 5% PEG-8000. After mixing the phases were allowed to separate during one hour and the upper phase which contained the beads was transferred to a column. Albumin was released from the beads by elution with 0.4M KSCN, and the yield was 85%.

3(f) Binding DNA to acridine yellow—polyacrylamide beads 50 μl of polyacrylamide beads with acridine yellow (DNA affinity gel, Boehringer Mannheim) and 50 μl of linear DNA from calf's thymus (Sigma) and plasmide DNA from *E. coli* (Sigma) were mixed with 900 μl of a phase system containing 10% Dextran T-70 and 7.0% PEG-8000. After mixing the phases were allowed to separate during 30 minutes, whereafter the PEG-phase which contained the beads was transferred to a column. Linear DNA was eluted with 0.2M $NaClO_4$ and plasmide DNA was eluted with 0.4M $NaClO_4$. The type of DNA and the purity were verified by electrophoresis (ethidium-bromide).

3(g) binding ATP to PEG-DEAE Sephacel®

DEAE Sephacel® (Pharmacia Fine Chemicals) was epoxy-activated in a manner analogous to that described in Example 1(f) and then PEG-4000 was coupled to the gel. 1.6 ml of settled gel suspension, 100 μl ATP-solution (adenosine 5′triphosphate, Sigma A-2383) containing 12.9 mg ATP and 600 μl 25 mM potassium phosphate buffer pH 7.1, were mixed with a phase system containing 7.3% PEG-4000 and 7.3% Dextran T500, dissolved in 25 mM potassium phosphate buffer, pH 7.1. The total amount was 12 g. The upper phase, which contained the gel particles, was transferred to a column after that the phases were separated. Bound ATP was then eluted with 1M NaCl in 25 mM potassium phosphate buffer, pH 7.1. The yield of ATP was 72.2% (9.3 mg).

3(h) Binding albumin to PEG-DEAE sephacel®

The gel was prepared in the same manner as in Example 3(g). During 30 minutes 12 g of settled gel suspension was mixed with 18 g of buffer (0.1M tris-HCl, 5 mM $MgCl_2$, 5 mM EDTA pH 8.2) and 540 mg bovine serum albumin (BSA, Sigma A-7030). PEG-4000 and Dextran T500 were added and a phase system of in total 180 g was formed (6% PEG and 7.2% dextran). The phases were separated within 10 minutes. The upper phase which contained the gel was transferred to a column, in which the gel was washed with a solution containing 50 mM tris, pH 7.5. Bound BSA was eluted with 1M NaCl dissolved in a tris-buffer, pH 7.5. The yield was 338 mg of BSA (62.6%) which corresponds to 28.1 mg of BSA per ml of gel.

EXAMPLE 4

Purification of alcohol dehydrogenase (ADH) and hexokinase from yeast 100 g of baker's yeast were degraded by vigorous agitation with glass beads in 40 ml of buffer pH 6.4 (0.020M Tris/HCl, 5 mM $MgCl_2$, 0.4 mM EDTA) for 8 minutes in a water-cooled vessel. Then followed additions of 20.0 g of Cibacron ® blue—methoxypolyethylene glycol—Sepharose ® 6B and another 30 ml of buffer so as to give a 150 ml total volume. The vessel was shaken for 2 hours. Thereafter polyethylene glycol 4000 (Merck) was added as well as an aqueous solution of $KH_2PO_4$ and $K_2HPO_4$ pH 7. This resulted in the formation of a two-phase system (phosphate 12%, polyethylene glycol 10.0%, distilled water 78%, total volume 900 ml).

The upper phase which contained the gel particles was transferred to an empty column (interior diameter 1.6 cm) provided with a bottom grid, the gel particles being then washed with buffer pH 6.4. The column was then connected to a chromatography system and eluted with 5 mM nicotinamide adenine dinucleotide (NAD, Sigma) in Tris buffer pH 6.4 (as above). Flow rate 14.5 ml/hour. ADH activity could be detected in fractions amounting to a total of 9 ml.

Purity was checked by electrophoresis in polyacrylamide gel (PAA 4/30 plates, Pharmacia Fine Chemicals, Sweden). When the pH was increased to 8.6 in the same buffer, hexokinase could be eluted from the gel particles. This enzyme was found to be present in fractions amounting to a total of 9 ml, and purity was checked by electrophoresis in the same was as above.

The above example thus involves purification of two enzymes naturally formed in yeast cells. Particles employed in practical applications of the invention may have a specific affinity for only one biologically active component or may have an affinity for a group of such components. In this latter case it is possible, as shown in the foregoing example, to employ suitable elution techniques in order to thus release one component at a time. The method is similarly applicable to the purification of substances that have been formed in a cell or organism carrying a DNA sequence that does not normally exist therein but has been introduced by for example recombinant DNA techniques.

EXAMPLE 5

Purification of transferrin from blood plasma

Coupling of PEG-4000 to Sepharose ® as well as CNBr activation was carried out as earlier described.

180 mg of anti-transferrin (BioCell, Uppsala, Sweden) was coupled to 15 g of activated gel by reaction during 2.5 hours on a rotory shaker and at 4° C. during the night without stirring. 140 mg of antibody was bound.

5 g of gel was mixed with 100 ml of human blood plasma and the mixture was left for 1.5 hours. Then PEG-4000 was added to a final concentration of 10% and potassium phosphate to a final concentration of 12%. The total weight was 295 g.

After that the phases were separated the upper phase containing the gel was transferred to a column where the gel was washed with 0.1M potassium phosphate, pH 7.0. Bound transferrin was eluted with 0.1M glycine-HCl, pH 3.0. The yield was 5.12 mg. Immunodiffusion and electrophoresis showed that the transferrin was immunologically active and clean.

We claim:

1. In a process for the purification of a biologically active substance with the aid of a system of at least two immiscible aqueous phases, the improvement that said substance is caused to bind to insoluble particles which have an affinity for said substance and distribute predominantly quantitative into one of said phases, and after separating the particle-containing phase from the other phase or the other phases, said substance is liberated from said particles.

2. A process according to claim 1, in which the biologically active substance is caused to bind to particles having a biospecific affinity for said substance.

3. A process according to claim 1, in which the biologically active substance is caused to bind to particles containing anion- or cation-exchanging groups.

4. A process according to claim 1, in which the particle-containing phase is passed down into a column provided with a bottom grid, whereupon the column with the particles thus retained is connected to a chromatographic system, washed and eluted with a solution by which the substance is liberated from the particles.

5. A process accordng to claim 2 in which the particle-containing phase is passed down into a column provided with a bottom grid, whereupon the column with the particles thus retained is connected to a chromatographic system, washed and eluted with a solution by which the substance is liberated from the particles.

6. A process according to claim 3 in which the particle-containing phase is passed down into a column provided with a bottom grid, whereupon the column with the particles thus retained is connected to a chromatographic system, washed and eluted with a solution by which the substance is liberated from the particles.

* * * * *